United States Patent [19]

Holmberg et al.

[11] Patent Number: 4,767,701
[45] Date of Patent: Aug. 30, 1988

[54] POLY I:C COVALENTLY BONDED TO POLYMER FOR DIAGNOSTIC PURPOSES

[75] Inventors: Krister Holmberg, Mölndal; Holger Hyden, Gothenburg, both of Sweden

[73] Assignee: Berol Kemi AB, Stenungsund, Sweden

[21] Appl. No.: 771,679

[22] Filed: Sep. 3, 1985

[51] Int. Cl.$^4$ ............... G01N 33/545; G01N 33/554
[52] U.S. Cl. .......................................... 435/7; 435/29; 435/34; 436/531; 436/532; 536/27
[58] Field of Search ............... 436/531, 532, 7, 29, 436/34; 536/27

[56] References Cited

U.S. PATENT DOCUMENTS

| | | | |
|---|---|---|---|
| 4,352,884 | 10/1982 | Nakashima | 436/531 X |
| 4,357,142 | 11/1982 | Schall | 436/531 |
| 4,362,697 | 12/1982 | Tabb | 436/531 X |
| 4,418,152 | 11/1983 | Hosaka | 436/531 X |
| 4,559,303 | 12/1985 | Aotani | 436/531 X |

OTHER PUBLICATIONS

Chemical Abstracts, I, 101:192407m (1984).
Chemical Abstracts, II, 101:235572f (1984).

*Primary Examiner*—Sidney Marantz
*Attorney, Agent, or Firm*—Spencer & Frank

[57] ABSTRACT

A carrier which consists of a carboxyl group-containing polymer, preferably activated polymethyl methacrylate, and on the surface of which a biologically active substance consisting of Poly I:C is immobilized, is described, as is a method of preparing such a carrier, and its use for diagnostic purposes. In the method of immobilizing Poly I:C on a carrier surface of polymethyl methacrylate, the surface of the polymethyl methacrylate carrier is first activated by treating it with strong alkali, such as a 10M sodium hydroxide solution. An aqueous solution of Poly I:C is heated, preferably for 1-2 h, and is then allowed to cool to about 50°-80° C., whereupon a coupler, preferably a water-soluble carbodiimide, is added to the solution. The warm solution is then applied to the activated carrier surface to immobilize Poly I:C on the carrier surface which then is allowed to cool to 0°-50° C.

17 Claims, No Drawings

POLY I:C COVALENTLY BONDED TO POLYMER FOR DIAGNOSTIC PURPOSES

The present invention relates generally to a carrier, on the surface of which a biologically active substance is immobilised and, more particularly, to a carboxyl-containing polymer surface, preferably an activated polymethyl methacrylate surface on which the biologically active substance Poly I, Poly C is immobilised. The invention also relates to a method for the preparation of such a carrier surface provided with immobilised Poly I:C, and to the use of such a carrier surface for diagnostic purposes.

Poly I, Poly C (abridged Poly I:C) is a synthetic polynucleotide consisting of a strand of polyriboinosinic acid (Poly I) and a strand of polyribocytidylic acid (Poly C). The two strands are held together by hydrogen bonds between purine and pyrimidine bases in the chains. The basic structure is similar to that of natural polynucleotides, such as DNA.

Poly I:C has been found to have a strong interferon-inducing effect in in vitro experiments, an observation that is highly interesting from the medical point of view since interferon is deemed to play an important part in the body's defence against certain diseases, for example certain forms of cancer.

However, the use of Poly I:C for clinical purposes has been limited for, inter alia, two reasons. In the first place, Poly I:C, if injected intravenously, is not stable but is degraded by nucleases in plasma. Furthermore, Poly I:C has been shown to cause toxic secondary effect on, inter alia, the liver and the kidneys.

The present invention also relates to a method of utilising immobilised Poly I:C for, for example, diagnostic purposes. Examples of suitable diagnostic applications are the supervision of patients suffering from autoimmune diseases and in the cytostatic treatment of cancer, in connection with organ transplantations, testing for AIDS, etc.

In the case of an infection and in the genesis of a tumour, it is of the utmost importance that one can diagnose the state of the specialised cells of the immunosystem and their ability to multiply and to be activated to produce their protective factors. This concerns in the first place the mononuclear cells in the peripheral blood which are effective producers of interferon (IFN-$\alpha$, -$\beta$ and -$\gamma$). A general rule is that interferon increases the growth and differentiation and stimulates the immunocells to exercise their protective effects and to produce protective substances.

The present invention makes it possible to diagnose the state of the immunosystem and the total ability of these specialised cells by contacting cell samples for a given period of time with the Poly I:C surface and then examining these samples for their ability to destroy and dissolve certain tumour cell types.

The most important mononuclear cell types capable of reacting to this diagnostic test are:
 T-lymphocytes which are effector cells for cell-mediated immunity and show cytotoxicity. They stimulate other white corpuscles towards maturation and, upon maturation, to produce IFN-$\alpha$ and -$\beta$.
 Natural killer cells (NK cells) which are large granular lymphocytes having, inter alia, tumour-destroying ability.
 B-lymphocytes which are precursors of antibody-producing cells. Some B cells produce INF-$\alpha$.
 Macrophages which are immunocells having a very broad function. They fagocytise and produce a number of immunofactors, complements, IFN-$\alpha$ and -$\beta$. Furthermore, they kill tumour cells in the activated state, and they treat antigen, which is a necessary step of the immunoprocess.

Interferon stimulates these cells in the normal immunosystem. The mechanism of this stimulation is complex, and a principal point is that the mononuclear cells of the blood themselves produce interferon when stimulated thereby. The present invention utilises this so-called positive self-control, it being possible to choose between studying, for example
 samples of mononuclear cells obtained by known technique,
 the total fraction of white corpuscles,
 herparinised blood.

Slurried in a suitable solution, the cells are contacted with the surface of immobilised Poly I:C. The activation, i.e. the contact with Poly I:C, is normally allowed to last several hours, whereupon the degree of activation and the cytotoxic effects of the immuno cells are determined on suitable cell lines, for example Molt-4, K-562 and Melanom RPMI 7931, which are NK-sensitive target cells suitable for quantitative determination according to known technique.

The invention is based on the principle that Poly I:C is immobilised by means of covalent bonds to a carrier surface with carboxyl groups. The carrier surface may be a carboxyl group-containing polymer or a polymer which, by activation, has been made to contain carboxyl groups, such as activated polymethyl methacrylate. Other suitable polymeric carrier materials are acrylate plastics containing, for example, acrylic acid or methacrylic acid as monomer, unsaturated polyester plastics and polyamide plastics.

In its simplest form, the carrier consists of small plates or rods which on one or more sides have Poly I:C immobilised on the surface.

As mentioned above, the carrier surface preferably consists of activated polymethyl methacrylate (PMMA), a material which is suitable from the practical/mechanical point of view since it resists the chemical and mechanical stress to which the thin plates are subjected. Furthermore, the hydrophobic plexiglas-brand PMMA surface is compatible with the blood and functions satisfactorily from the viewpoint of sterilisation.

However, a PMMA surface is chemically inert and therefore is difficult to use as a carrier material when covalent bonds are required. (This aversion to participating in chemical reactions is one of the reasons for its excellent biocompatibility.) It has been found, however, that treatment with alkaline solution makes it possible to activate the surface by partial hydrolysis of methyl ester groups in the surface, whereby carboxyl groups are formed which, theoretically, should be able to serve as anchoring groups upon immobilisation of a biologically active substance. More particularly, the surface is activated by treating it with an alkali metal hydroxide solution, preferably a 2-15M sodium or potassium hydroxide solution. The temperature of the activation treatment is not critical, but lies preferably within the range of about 10°-100° C.

Immobilisation of biologically active substances to carboxyl functional carriers is previously known in and per se and is used, inter alia, for enzymes and other proteins. Covalent immobilisation of double-stranded polynucleotides, such as Poly I:C, on the other hand is complicated and, as far as is known, has not been described in literature. All known immobilisation techniques aiming at providing covalent bonds require, in the biologically active substance, some functional group which either directly or via a linkage can be made to couple to the functional group of the carrier material. As mentioned above, Poly I:C has amino groups in purine and pyrimidine bases which in and per se could be made to react with carboxyl groups in the surface of the carrier polymer but which, in actual practice, are entirely inert because they are utilised in hydrogen bonds between the chains.

The literature discloses some examples of experiments aiming at bonding Poly I:C to carrier surfaces. The coupling techniques employed are conventional and seem to provide no complete covalent bond of the polynucleotide with retained activity. A fairly recent summary report on the subject (P. Pitha, Methods in Enzymology 78 (1981) 236) concludes: "The experiments in which immobilised Poly I:C was used demonstrated that Poly I:C coupled to carrier has antiviral activity. However, in all experiments the leakage of the Poly I:C from the carrier into the medium or its association with the cells were observed . . . The use of immobilised inducers is limited by the leakage of the inducer from the carrier".

For further information regarding the immobilisation of Poly I:C, reference should be made in this connection also to Chemical Abstracts 83(1975):191244d and 82(1975):137578g. Regarding the use of PMMA as a carrier for immobilisation, mention should be made of Chemical Abstracts 82(1975):103117r and Arzneim.-Forsch., 21(11), 1971, pp. 1671-5.

It has now surprisingly proved possible to provide an immobilisation of Poly I:C to a carboxyl-functional carrier surface by first heating a solution of the polynucleotide and then adding the solution, while allowing it to cool, together with a water-soluble coupler to the carrier. The heating time and the temperature are not critical, but a time between 5 min. and 4 h and a temperature of 70°-100° C. seem suitable. Naturally, a lower temperature requires a longer time, and vice versa. At present, heating to 90°-100° C. for 1-2 h is preferred. Before the coupler is added to the polynucleotide solution, the solution usually should be allowed to cool somewhat. A suitable temperature for the addition is 50°-100° C., preferably 50°-80° C. While the solution is still warm, it is added to a carboxyl-containing carrier surface to immobilise the polynucleotide on the carrier surface by means of the coupler which either may be added first to the polynucleotide solution or added separately to the carrier. Various couplers capable of coupling an active substance to a carrier by forming covalent bonds are previously known in the art. In the present invention, the preferred coupler is a water-soluble carbodiimide, preferably 1-(3-dimethylaminopropyl)-3-ethyl carbodiimide or 1-cyclohexyl-3-(2-morpholinoethyl)carbodiimide.

After the carrier has been treated with the polynucleotide solution and the coupler, the carrier surface is allowed to cool to a temperature of about 0°-50° C., preferably about 0°-25° C.

The reaction mechanism of this immobilisation technique has not been explained, but one theory is that the two polynucleotide strands upon heating at least partly separate into individual polymer chains. The water-soluble carbodiimide then makes it possible to form amide bonds between primary amino groups in the cytosine of the poly C chains and carboxyl groups on the carrier surface. The double-stranded structure is then at least partly reformed upon cooling, i.e. the poly I chains are withdrawn from the solution and again bonded by means of hydrogen bonds to the immobilised complementary strand. As will appear from the following Examples, the biological effect of the immobilised polynucleotide is excellent, which should imply that the original conformation of the double strand has largely been reformed.

So far as is known, the present method of immobilising a double-stranded polynucleotide has not previously been described. The method deviates considerably from prior art technique, and its possibilities of being successful must be regarded a priori as rather poor. If a thermal treatment causes the structure to be split up into two chains, and one of these chains is then bonded to a carrier surface, it may seem peculiar that the other chain largely resumes its position upon cooling. In other polynucleotides that have been investigated, for example DNA, not even the thermal splitting is entirely reversible, i.e. the structure (and thus the biological effect) is not reformed after boiling, not even if the subsequent immobilisation is omitted.

ESCA analysis of the carrier plates (PMMA) has been carried out to ensure that the polynucleotide has indeed been bonded to the surface. An attempt at leaching Poly I:C by means of flowing salt solution after immobilisation failed completely.

The following Examples are intended to illustrate the invention without restricting its scope.

EXAMPLE 1

A solution of Poly I:C in water (10 mg in 250 ml) is reflux-boiled for 1 h. After cooling to 70° C., 1-(3-dimethylaminopropyl)-3-ethyl carbodiimide, hydrochloride (1.5 g) is added. The homogeneous solution is added to a surface of PMMA which before then has been treated with 10M of NaOH to generate COOH groups on the surface. The solution which still has a temperature of 70° C. when supplied to the surface, is allowed to cool slowly to 4° C. under continuous circulation. After 16 h, immobilisation is complete.

Blood from two patients, one suffering from AIDS, and the other suffering from both AIDS and Kaposi's sarcoma, was incubated for 2 h in a chamber with walls of PMMA on whose surfaces Poly I:C had been immobilised as indicated above. Samples of the mononuclear cells of the blood were tested prior to and after incubation for cytotoxic activity against melanoma cells RPMI 7931. The patient which suffered from AIDS only, showed toxicity values of <10% prior to incubation and 80% after incubation. The corresponding values of the patient suffering from both AIDS and Kaposi's sarcoma were 5 and 20%, respectively.

The insignificant rise in cytotoxicity for the latter patient is a measure of a larger defect in the immunodefence of this patient.

EXAMPLE 2

A solution of Poly I:C in water (10 mg in 250 ml) is heated to 90° C. for 2 h. After cooling to 60° C., 1-cyclohexyl-3-(2-morpholinoethyl)carbodiimide is added. A plate of polymethyl methacrylate previously treated with 8M of KOH to generate COOH groups on the surface, is immersed in a homogeneous solution.

The solution is allowed to cool to 6° C. After 16 h, immobilisation is complete.

The activity of the immunosystem, reflected in cytotoxicity of mononuclear cells of the peripheral blood, was examined in a patient suffering from malignant lymphoma during one week's treatment with Sendoxan (cyclophosphamide). Incubation of cells samples was carried out daily after each Sendoxan treatment. Upon incubation, the cells were contracted with PMMA plates on the surface of which Poly I:C had been immobilised as indicated above. The cytotoxicity was determined against cell line Molt-4. The value prior to the cytostatica treatment was 60%. The cytotoxicity values measured prior to and after incubation with Poly I:C on the days during which the Sendoxane therapy was carried out, will appear from the following Table.

TABLE

| Therapy day No. | Cytotox. before | Cytotox. after |
|---|---|---|
| 1 | 50% | 65% |
| 2 | 25% | 35% |
| 3 | 20% | 20% |
| 4 | 10% | 10% |
| 5 | 0% | 0% |

As can be seen, the Poly I:C incubation causes no rise in cytotoxicity as from day No. 3. According to the diagnostic method employed, the immunosystem of the patient thus has been eliminated, i.e. the immunodefence has largely lost its ability to be activated.

What we claim and desire to secure by Letters Patent is:

1. A carrier of carboxyl group-containing polymer with covalently immobilised biologically active Poly I:C.

2. A carrier as claimed in claim 1, wherein the carboxyl group-containing polymer is activated polymethyl methacrylate.

3. A method of immobilising biologically active Poly I:C on a carrier of carboxyl group-containing polymer, comprising:
adding an aqueous solution of biologically active Poly I:C at a temperature of 50°-100° C. and a coupler in the form of a water-soluble carbodiimide to the surface of a carboxyl group-containing polymer,
cooling said carrier surface to 0°-50° C., and
covalently immobilising said biologically active Poly I:C on said carrier surface.

4. A method as claimed in claim 3, wherein the carrier polymer is polymethyl methacrylate, the surface of which is activated to form carboxyl groups by treatment with an alkaline solution at a temperature of 10°-100° C.

5. A method as claimed in claim 4, wherein the polymethyl methacrylate surface is activated with an alkali metal hydroxide solution.

6. A method as claimed in claim 3, wherein the aqueous solution of Poly I:C is heated for a period of time from about 5 min. to about 4 h.

7. A method as claimed in claim 3, wherein the aqueous solution of Poly I:C is heated to a temperature of between 70° and 100° C.

8. A method as claimed in claim 3, wherein the aqueous solution of Poly I:C has a temperature of about 50°-80° C. when added to the carrier surface together with the coupler.

9. A method as claimed in claim 3, wherein 1-(3-dimethylaminopropyl)-3-ethyl carbodiimide, hydrochloride or 1-cyclohexyl-3-(2-morpholinoethyl)carbodiimide is added as the coupler.

10. A method of testing an immunosystem by contacting a blood sample with the carrier as claimed in claim 1, for diagnostic purposes.

11. The method as claimed in claim 10, including determining T-lymphocytes in said blood sample.

12. The method as claimed in claim 10, including determining natural killer cells in said blood sample.

13. The method as claimed in claim 10, including determining B-lympocytes in said blood sample.

14. The method as claimed in claim 10, including determining macrophages in said blood sample.

15. The method as claimed in claim 10, wherein said blood sample comprises heparinised blood.

16. The method as claimed in claim 10, wherein said blood sample comprises a total fraction of white corpuscles.

17. The method as claimed in claim 10, wherein said blood sample comprises mononuclear cells.

* * * * *